(12) United States Patent
Gumbrecht et al.

(10) Patent No.: US 8,551,737 B2
(45) Date of Patent: Oct. 8, 2013

(54) METHOD FOR ANALYSING AMPLIFIED NUCLEIC ACIDS

(75) Inventors: Walter Gumbrecht, Herzogenaurach (DE); Peter Paulicka, Erlangen (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 691 days.

(21) Appl. No.: 12/308,552

(22) PCT Filed: May 31, 2007

(86) PCT No.: PCT/EP2007/055335
§ 371 (c)(1),
(2), (4) Date: Jan. 14, 2009

(87) PCT Pub. No.: WO2007/147712
PCT Pub. Date: Dec. 27, 2007

(65) Prior Publication Data
US 2010/0009864 A1    Jan. 14, 2010

(30) Foreign Application Priority Data

Jun. 19, 2006   (DE) .................. 10 2006 028 101

(51) Int. Cl.
*C12P 19/34*   (2006.01)
*C12Q 1/68*   (2006.01)

(52) U.S. Cl.
USPC .......................................... 435/91.2; 435/6.1

(58) Field of Classification Search
USPC .................................. 435/91.2, 6.1
See application file for complete search history.

(56) References Cited

U.S. PATENT DOCUMENTS

| | | | |
|---|---|---|---|
| 4,683,195 A | | 7/1987 | Mullis et al. |
| 5,783,685 A | * | 7/1998 | Bahl et al. ................... 536/25.3 |
| 6,440,725 B1 | * | 8/2002 | Pourahmadi et al. ....... 435/288.5 |
| 2003/0213006 A1 | * | 11/2003 | Back et al. ........................ 800/8 |
| 2004/0007275 A1 | | 1/2004 | Bonanno |
| 2004/0063152 A1 | | 4/2004 | Gumbrecht et al. |
| 2004/0115094 A1 | | 6/2004 | Gumbrecht et al. |
| 2008/0305966 A1 | * | 12/2008 | Peytavi et al. ................... 506/16 |

FOREIGN PATENT DOCUMENTS

| | | |
|---|---|---|
| DE | 10 058 397 | 6/2002 |
| DE | 10058397 | 6/2002 |
| DE | 10 126 341 | 12/2002 |
| DE | 10126341 | 12/2002 |
| DE | 102005049976 A1 | 4/2006 |
| NE | 10111457 A1 | 9/2002 |

OTHER PUBLICATIONS

PCT/ISA/220 German Office Action.
G.Gassen, G.Schrimpf; Gentechnische Methoden; Spektrum akademischer Verlag heidelberg, 1999, Seiten 243 bis 261; Others; 1999.
Walker, GT et al.; Strand Displacement Amplification, an isothermal, invitro DNA Amplification Technique; Nucleic Acids Research, 1992, 20, 1961 bis 1996, durch TMA (transcription mediated amplification) www.gen-probe.com/sci_tech/tma.htm; Others.
Bertina et al.: "Mutation in blood coagulation factor v associated with resistance to activated protein c" Nature 369, 1994 pp. 64-67; Others; 1994.
Robin Hui Liu et al., "Integrated microfluidic biochips for DNA microarray analysis", Expert Review of Molecular Diagnostic Mar. 2006, Bd. 6, Nr. 2, Mar. 2006, Seiten 253-261, XP009087908, ISSN: 1744-8352; Others; 2006.
Zhang et al., "PCR microfluidic devices for DNA amplification", Biotechnology Advances, Elsevier Publishing, Barking, GB, Bd. 24, Nr. 3, May 2006, Seiten 243.284, XP005362290, ISSN: 0734-9750, das ganze Dokument, insb. Abschnitt 8.2; Others; 2006.
Umek et al.: "Electronic Detection of Nucleic Acids—A Versatile Platform for Molecular Diagnostics" J. Mol. Diagnost. vol. 3, No. 2 pp. 74-84; Others.
Liu Robin Hui et al.: "Self-contained, fully integrated biochip for sample preparation, polymerase chain reaction amplification, and DNA microarray detection" Analytical Chemistry, American Chemical Society, Columbus, US vol. 76, Nr. 7, Apr. 1, 2004 pp. 1824-1831 XP001196720 ISSN: 003-2700; Others.
Peytavi et al.: "Microfluidic device for rapid (<15 min) automated microarray hybridization" Clin. Chem. (2005) 51 (10) pp. 1836-1844; Others.
Xia et al.: "Nested coamplification polymerase chain reaction" Article from Journal: Zhonghua Yi Xue Yi Chuan Xue Za Zhi (2002) 19 (4) pp. 347-349 Abstract on PubMed under www.ncbi.nlm.nih.gov; Others.
Gerstein, A. "Molecular Biology Problem Solver: A Laboratory Guide" ISBN: 0-471-37972-7; 2001, pp. 428-430: Others; 2001.

* cited by examiner

*Primary Examiner* — Cynthia Wilder
(74) *Attorney, Agent, or Firm* — Harness, Dickey & Pierce, P.L.C.

(57) ABSTRACT

An example embodiment of the present invention discloses a method for analyzing nucleic acids in a microfluidic device. The method includes the following steps: a) nucleic acids are amplified in a first chamber in the microfluidic device; b) the amplified nucleic acids are brought into contact with an additive including: i) monovalent cations and ii) an Mg2+ ion-binding agent, the additive being provided in a second chamber in the microfluidic device; and c) the amplified nucleic acids are hybridized on at least one probe oligonucleotide.

17 Claims, 4 Drawing Sheets

METHOD FOR ANALYSING AMPLIFIED NUCLEIC ACIDS

PRIORITY STATEMENT

This application is the national phase under 35 U.S.C. §371 of PCT International Application No. PCT/EP2007/055335 which has an International filing date of May 31, 2007, which designated the United States of America and which claims priority on German application No. 10 2006 028 101.2 filed Jun. 19, 2006, the entire contents of which are hereby incorporated herein by reference.

FIELD

At least one embodiment of the invention generally relates to a method for analyzing amplified nucleic acids in a microfluidic device. At least one embodiment of the invention furthermore generally relates to an arrangement for carrying out at least one embodiment of such a method.

BACKGROUND

DNA analysis by hybridization is a known method in molecular biology (cf. "Gentechnische Methoden", ["Genetic Engineering Methods"], G. Gassen and G. Schrimpf, Spektrum Akademischer Verlag Heidelberg, 1999, pages 243 to 261). This technique plays an important part in the detection of specific nucleic acids, e.g. in the molecular diagnosis of single point mutations (single nucleotide polymorphism, SNP). In this case, a probe oligonucleotide comprising a sequence of e.g. approximately 20 nucleotides is used to bind to nucleic acids that differ only in a single nucleotide. It is noted that in the present context the expression "nucleic acids" is intended to encompass a nucleic acid sequence, e.g. a DNA sequence or RNA sequence. Given a suitable choice of the hybridization conditions (in particular temperature and salt concentration), the probe oligonucleotide selectively binds the non-mutated variant of the nucleic acid, while the nucleic acid variant having the single point mutation does not bind, or binds only weakly. Detection of single point mutations is thereby possible. On account of the small differences in terms of binding energy between the variant without a mutation (that is to say the wild type) and the mutant, the reaction conditions with regard to temperature and also composition and salt concentration of the reaction solution have to satisfy exact stipulations.

Since the corresponding nucleic acids in the sample material (e.g. blood) are usually not available in sufficient quantity or concentration, it is necessary to amplify the nucleic acids to be examined. This amplification can be effected in a sequence-specific manner by various methods known in molecular biology, e.g. by SDA (strand displacement amplification), described in Walker, G T, et al., "Strand Displacement Amplification, an isothermal, in vitro DNA Amplification Technique", Nucleic Acids Research, 1992, 20, 1961 to 96; by TMA (transcription mediated amplification), described in www.gen-probe.com/sci_tech/tma.htm; or by polymerase chain reaction (PCR), described in U.S. Pat. No. 4,683,195, inter alia. One problem here is that the composition of the reaction solution of the amplification reaction, and hence the "amplification crude product", does not have the composition, and in particular salt concentrations, required for hybridization. For molecular diagnosis, it may additionally be necessary to selectively separate the hybrids formed in a subsequent process (melting) e.g. by increasing the temperature. In order to enable hybridization processes with a high yield, a high concentration of monovalent cations (e.g. $Na^+$ ions) is necessary, inter alia. Monovalent cations promote the formation of the double helix structure during the hybridization reaction.

However, the reaction mixtures of the amplification reactions, e.g. for a PCR reaction, contain a low concentration of monovalent cations. Furthermore, PCR reaction buffers have a relatively high concentration (a few mM) of $Mg^{2+}$ ions, which, during the hybridization to detection probes, adversely affect the binding of probes and complimentary strands to form complete hybrids, can bring about an extension of the probes by polymerase activity and, during a subsequent melting process, bring about a stabilization of double strands and make melting more difficult, which leads to "washed out" melting curves at high temperatures.

In accordance with the prior art, amplification products are therefore purified before the hybridization reaction; in this case, all components that disturb a hybridization reaction (inter alia polymerase, primers, nucleotides, salts) are removed and the concentration of $Na^+$ ions is increased. This purification process is relatively complicated and is usually effected by non-specific binding of the nucleic acids to a solid phase (by way of so-called purification columns), washing of the amplification product on the column and dissolution from the solid phase or by phenol/chloroform extraction or similar methods. Particularly when carrying out nucleic acid analyses in microfluidic devices, wherein all the reaction processes proceed in an integrated manner and in a small space, the purification methods that are customary in the prior art are not appropriate since their realization is too complicated, under these circumstances.

SUMMARY

At least one embodiment of the present invention provides a simple and cost-effective method which enables the efficient conditioning of amplified nucleic acids for further method steps, requires no additional binding or washing steps and can be realized with a simple fluidics concept.

Expressed in general terms, the concept of at least one embodiment of the invention resides in amplifying a sample with nucleic acids and admixing the sample containing the amplification crude product with a suitable additive in order to condition the amplification crude product for further method steps, e.g. further analysis steps. Adding the additive avoids the need to purify the amplified nucleic acids. This method is particularly suitable for use in microfluidic devices, in which uncomplicated method sequences with a simple fluidics concept are preferred. According to at least one embodiment of the invention, the additive comprises monovalent cations and an $Mg^{2+}$ ion-binding agent. Such an additive is suitable in particular for conditioning amplified nucleic acids for a subsequent hybridization to probe oligonucleotides.

At least one embodiment of the present invention provides, in particular, a method for analyzing amplified nucleic acids in a microfluidic device, comprising the following steps:
a) amplifying nucleic acids in a first chamber in the microfluidic device;
b) contacting the amplified nucleic acids with an additive, comprising:
   i) monovalent cations and
   ii) an $Mg^{2+}$ ion-binding agent,
   wherein the additive is provided in a second chamber in the microfluidic device; and
c) hybridizing the amplified nucleic acids to at least one probe oligonucleotide.

The expression "microfluidic" denotes methods which comprise the handling of fluids having volumes in the microliters range. The microfluidic device is preferably embodied as a cartridge, that is to say as a flat structure having the form of a card, with depressions formed therein which form channels and chambers or cavities through which liquids can be moved in accordance with predetermined reaction sequences or schemes.

Monovalent cations comprise e.g. $Li^+$, $Na^+$, $Ka^+$, and are present in the additive according to the invention preferably in the form of $Na^+$ ions. An $Mg^{2+}$ ion-binding agent should be understood to mean all substances that bind $Mg^{2+}$ ions, in particular complexing agents, e.g. Chelate complexing agents such as EGTA or EDTA. The additive used in the method according to the invention preferably comprises EDTA. Furthermore, the additive preferably comprises a binder, e.g. polyvinylpyrrolidone. Further auxiliaries, e.g. buffer substances, surface-active substances, or the like, can likewise be provided.

In accordance with one preferred aspect of at least one embodiment of the invention, the additive in the second chamber is provided as a dry reagent and is kept therein in storage-stable fashion.

Preferably, the probe oligonucleotides are immobilized as a microarray on a carrier in the microfluidic device.

In accordance with a first embodiment of the method of the present invention, the additive is transferred from the second chamber to the first chamber (the amplification chamber) in order to contact the additive with the amplified nucleic acids. If the additive is provided as a dry reagent in the second chamber in this embodiment of the method according to the invention, it is expedient to dissolve the additive using a solvent, e.g. water. The dissolved additive can then be transferred from the second chamber to the first chamber in order to be mixed there with the amplification crude product.

In accordance with a second embodiment of the present invention, after amplification has been effected, the amplified nucleic acids in the reaction solution are transferred from the first chamber to the second chamber and then conducted as a mixture with the additive to the probe oligonucleotides. If the additive is provided as a dry reagent in the second chamber, it can be dissolved directly by the reaction solution pumped into the second chamber with the amplification crude product.

According to at least one embodiment of the invention, it is preferred for the nucleic acids to be amplified by PCR reaction.

In accordance with a further aspect of at least one embodiment of the present invention, the amplified nucleic acids hybridized to the probe oligonucleotides are then preferably detected. This detection can be effected for example using a label (a marking) of the amplified nucleic acids. The label can be an optical label; it can also be an enzymatic label, for example. An enzymatic reaction can be catalyzed by an enzymatic label, which reaction can be detected e.g. optically or electrochemically. According to the invention, preferably an electrochemical detection is carried out, which particularly preferably comprises a current measurement amplified by way of redox cycling.

In particular, at least one embodiment of the invention furthermore relates to an arrangement for carrying out the method according to at least one embodiment of the invention, which is provided in a microfluidic device, comprising a first chamber, which is designed for the amplification of nucleic acids, and a second chamber, in which the additive described above is kept in storage-stable fashion, wherein the second chamber can be connected in fluid communication via a connection to the first chamber. Preferably, the arrangement comprises a microarray arrangement having probe oligonucleotides immobilized on a carrier.

The connection between the first and second chambers can be embodied in the form of a line or a channel, and can preferably be selectively opened and closed, e.g. by way of a valve, such that fluid can selectively be transferred from the first to the second chamber, or from the second to the first chamber. Furthermore, device(s)/method(s) can be provided for introducing a solvent into the second chamber, e.g. in the form of an inlet channel to the second chamber.

Preferably, the microarray arrangement is assigned device(s)/method(s) for detecting hybridized nucleic acids, which enable an optical or electrochemical detection, for example. Electrochemical detection device(s) which are designed for measuring currents and/or potentials are particularly preferred. The optical detection device(s) can comprise e.g. a transparent region of the device, through which e.g. optical absorption or fluorescence excitation and detection can be read out. The electrochemical detection device(s) preferably enable the measurement of potentials and/or currents and can comprise an electrode system onto which the probe oligonucleotides are immobilized (spotted) at each detection spot, as described for example in the documents DE 101 26 341 A1 or DE 100 58 397 A1, the entire contents of each of which are hereby incorporated herein by reference.

Furthermore, corresponding device(s))/method(s), e.g. in the form of corresponding chambers and/or channels, can be provided for storing and/or passing on reagents for the detection, e.g. enzyme or enzyme substrate, in the microfluidic device.

Device(s)/method(s) for supplying heat and/or dissipating heat are preferably assigned to the first chamber (that is to say the amplification chamber). The device(s)/method(s) can comprise a region having increased thermal conductivity in the microfluidic device, which region can be realized for example by the microfluidic device being embodied in particularly thin-walled fashion in said region. However, it is also conceivable for an element that generates or dissipates heat to be provided in the microfluidic device itself.

BRIEF DESCRIPTION OF THE DRAWINGS

Further features and advantages of the present invention will become apparent from the following description of figures in association with the exemplary embodiments and with reference to the appended drawings, which are merely by way of example and illustrative.

In the figures.

DETAILED DESCRIPTION OF THE EXAMPLE EMBODIMENTS

Figure 1:
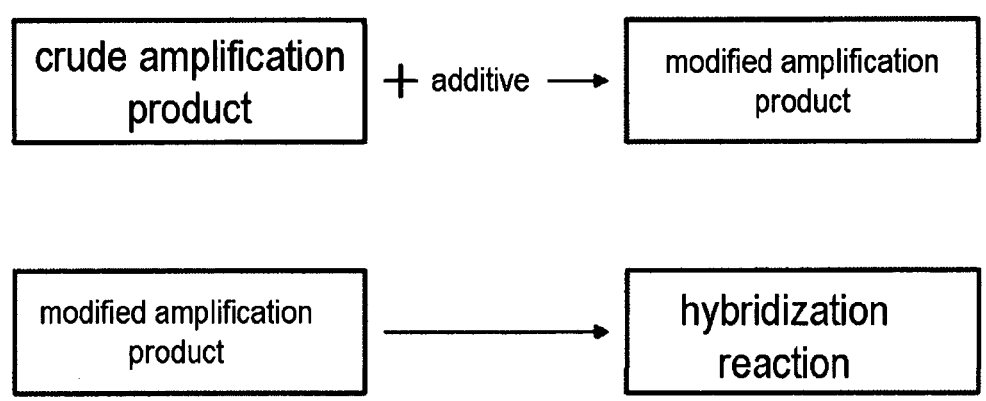
FIG. 1 shows a diagrammatic illustration of the method according to an embodiment of the invention.

FIG. 1 schematically illustrates the basic concept of the method according to an embodiment of the invention for analyzing nucleic acids in a microfluidic device. In accordance with the prior art it is known to purify amplification crude products prior to hybridization. This constitutes a subtractive method, that is to say that disturbing components (polymerase, primers, nucleotides) are removed from the solution containing the amplification crude product. By contrast, the method according to an embodiment of the invention is an additive method, that is to say that an additive is added to the amplification crude product, which additive enables an improved hybridization reaction, or a subsequent improved, selective separation of the hybrids. In this case it is unimportant whether the additive is added to the amplification crude product or the amplification crude product is added to the additive; what is crucial primarily is that a mixture of amplification crude product and additive is used for the hybridization reaction.

Figure 2:
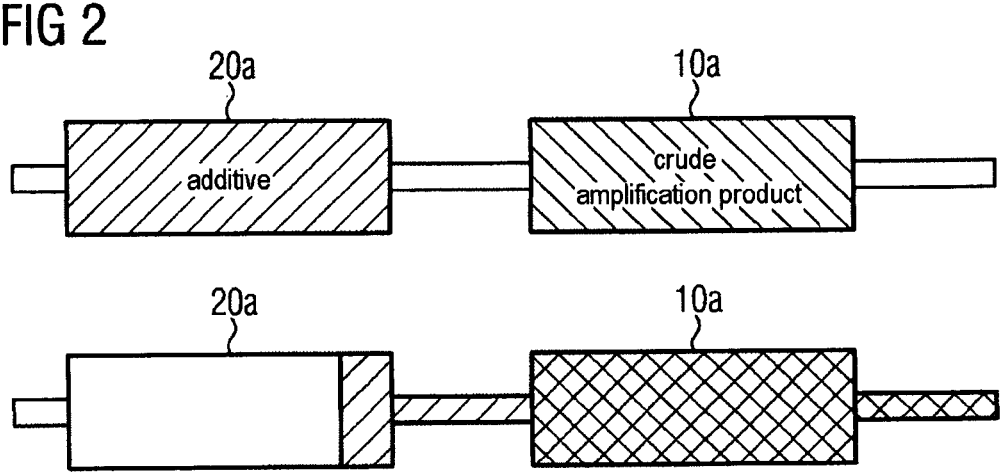
FIG. 2 shows a schematic illustration of an arrangement for carrying out the method of the invention in accordance with a first embodiment.

FIG. 2 shows an arrangement for carrying out the method according to an embodiment of the invention in accordance with a first embodiment with a first chamber 10a and a second chamber 20a. After the amplification reaction has taken place, the additive in solution is pumped from the second chamber 20a (the additive chamber) into the first chamber 10a (the amplification reaction chamber). If the additive in the second chamber is provided as a dry reagent, firstly a solvent (water) is pumped into the second chamber 20a in order to dissolve the dry reagent, and then the solvent is transferred to the first chamber 10a (amplification reaction chamber).

Figure 3:
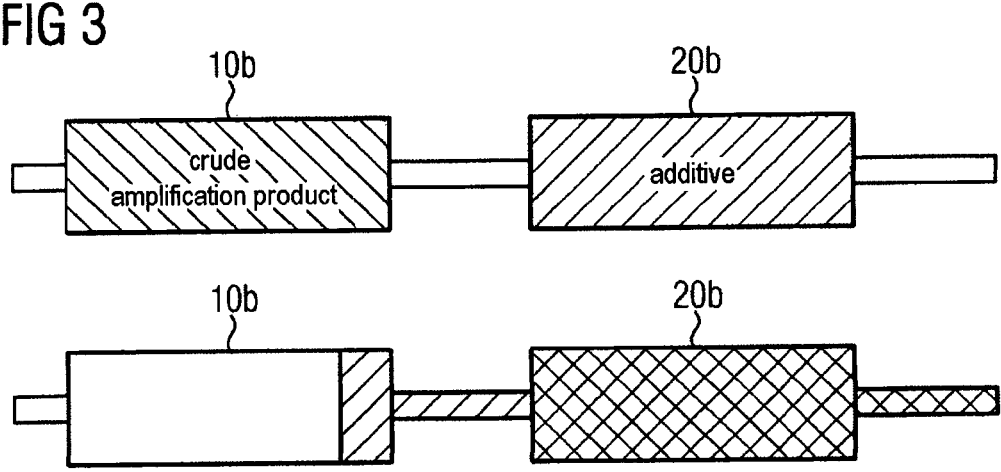
FIG. 3 shows a schematic illustration of an arrangement for carrying out the method of the invention in accordance with a second embodiment.

FIG. 3 shows an arrangement for carrying out the method according to an embodiment of the invention in accordance with a second embodiment with a first chamber 10b and second chamber 20b. In this case, the opposite procedure to the method implementation described above takes place: after the amplification reaction, the amplification crude product is conducted from the first chamber 10b (the amplification reaction chamber) into the second chamber 20b (the additive chamber) and intermixed there with the additive. If the additive is present as a dry reagent, the amplification crude product is pumped over the dry reagent and dissolves the latter.

In both embodiments, the mixture of amplification crude product and additive is then transferred to the microarray for hybridization.

Figure 4:
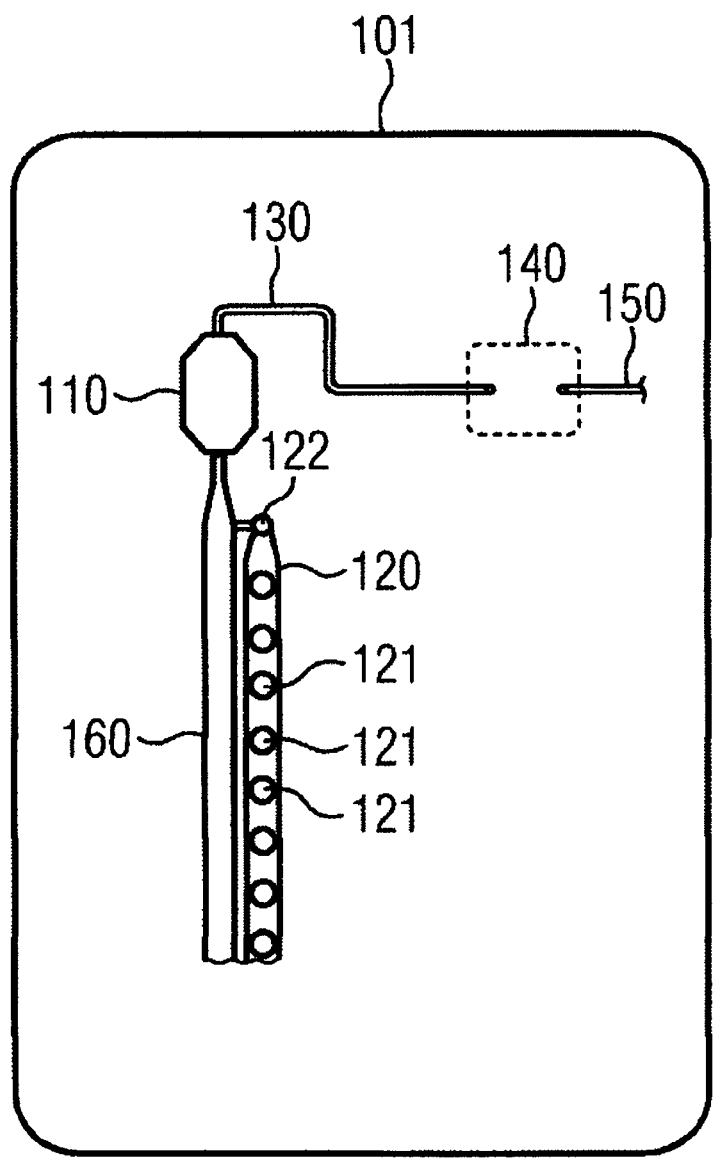
FIG. 4 shows an excerpt from a schematic illustration of a cartridge with the arrangement in accordance with FIG. 2.

FIG. 4 shows an arrangement in accordance with the embodiment shown in FIG. 2. FIG. 4 shows a cartridge 101, made from a plastic material. Channels 130, 150, 160, chambers 110, 120, 140 and depressions 121 are provided in the cartridge 101. The plastic cartridge can be embodied simply with upwardly open channels, depressions and chambers and can be covered with a film after the reagents have been spotted on, whereby the channels, depressions and chambers incorporated into the surface of the cartridge are closed off. In the first chamber 110, which can be filled via the inlet channel 160, nucleic acids are amplified by PCR reaction, for example. This is done by inserting the cartridge into a corresponding device, such that the chamber 110 can be heated and/or cooled, e.g. by Peltier elements situated in the device. The additive, comprising EDTA and sodium chloride, is present as a dry reagent in the depressions 121 in the second chamber 120, which is embodied as a channel. At one of its ends, the chamber 120 can be closed by a valve 122. This can be embodied for example as a simple pinch valve.

After the PCR reaction has taken place, water is pumped into the chamber 120, and the additive stored as a dry reagent is thereby dissolved. Afterward, the valve 122 is opened and the dissolved additive can then be pumped into the amplification chamber 110, where the dissolved additive intermixes with the amplification crude product, and the mixture is then pumped via the channel 130 into the hybridization chamber 140, in which a microarray with probe oligonucleotides immobilized on a carrier is provided. By a suitable choice of the fluidics, e.g. geometry or flow rates, it is possible to realize the effect whereby firstly unchanged amplification product is conveyed at the beginning of the pumping process and additive substances are increasingly admixed only upon further pumping. Consequently, a possibly advantageous rising concentration gradient of additive substances can be pumped into the hybridization chamber. The hybridization reaction can then take place in this chamber. Excess solution is fed via the outlet channel 150 to a waste container. Further chambers and channels can be provided (not shown) on the cartridge in order e.g. to keep ready reagents for the detection of the bound nucleic acids, such as, for instance, enzyme or enzyme substrate.

Example

Figure 5:
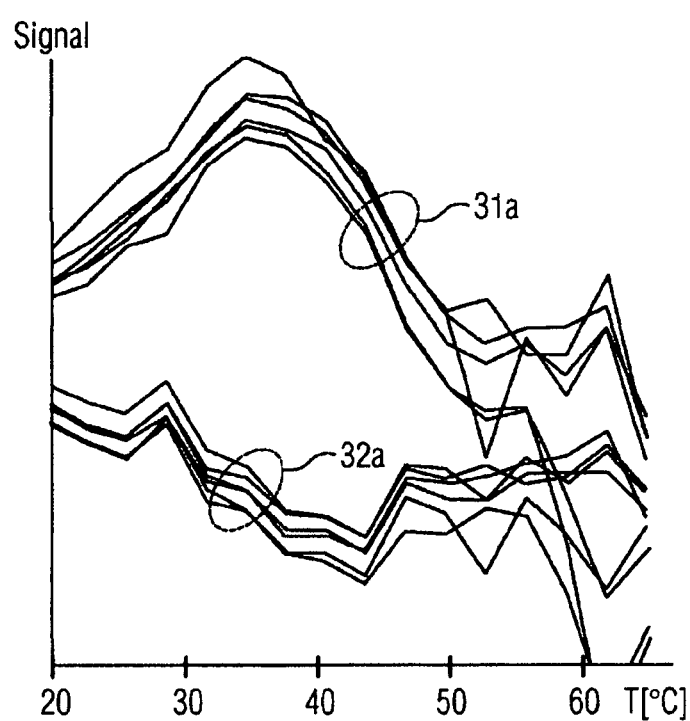
FIG. 5 shows a comparative illustration of melting curves of hybridized nucleic acids without the use of the method according to an embodiment of the invention.
Figure 6:
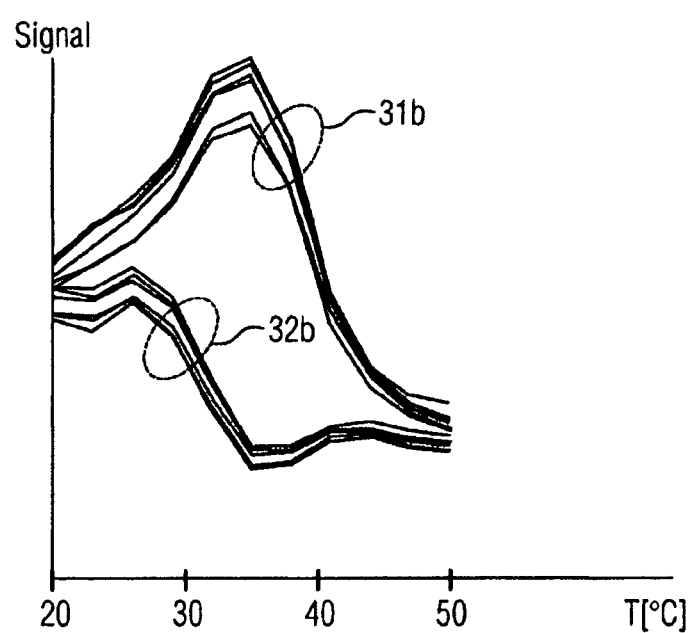
FIG. 6 shows a comparative illustration of melting curves of hybridized nucleic acids with the use of the method according to an embodiment of the invention.

An injection-molded plastic card of the type shown in FIG. 4 was used for recording the curves shown in FIGS. 5 and 6, in which card dry reagent was spotted on in the depressions 121. In order to evaluate the method according to an embodiment of the invention, the gene factor V wild type (FcV wild type) and the single point mutation factor V Leiden (FcV Leiden) were amplified by PCR so as to obtain a PCR product having a size of 168 bp. The gene product of the factor V gene is a protein of the blood coagulation cascade, and the mutation is described in Bertima et al., Nature, 1994; 369(6475): 64-7, the entire contents of which are incorporated herein by reference.

The DNA sample is introduced into the first chamber (amplification chamber) 110 and the PCR reaction is carried out. The channel 120 with the depressions 121 is filled with water, and the dry reagent is thereby dissolved. The additive spotted on as a dry reagent is dimensioned such that a solution comprising 0.23M NaCl, 0.1M EDTA results upon addition of approximately 25 µl of water. This ensures a sufficient concentration of monovalent cations and the minimization of the concentration of free $Mg^{2+}$ by complexing.

Furthermore, a buffer substance is added to the additive, such that the solution is adjusted to a pH value of pH=8. After the end of the PCR reaction, as a result of the dissolved additive flowing into the first chamber 110, the PCR crude product (amplification crude product) is mixed with the additive, and the mixture is forwarded into the chamber 140, in which a microarray arrangement is situated. Biotinylated PCR products are obtained by using biotinylated primers during the PCR reaction.

Probe oligonucleotides which can be used to discriminate between FcV wild type and FcV Leiden are spotted on the microarray arrangement. The probe oligonucleotides are chosen such that some spots carry probe oligonucleotides which perfectly match FcV wild type, while other spots carry probe oligonucleotides which perfectly match FcV Leiden. If the PCR product contains FcV wild type sequences, for example, then they form a "perfect match" (a complete pairing of strand and counter strand) with the wild type probes, but a "single base mismatch", having a lower binding strength, with the FcV Leiden probes. The PCR products bound to probe molecules are rinsed with a washing solution containing a streptavidin-conjugated enzyme (alkaline phosphatase). The enzyme binds to the biotinylated PCR products bound on the microarray arrangement.

The microarray arrangement is then rinsed with a substrate solution containing p-aminophenyl phosphate. The p-aminophenyl phosphate is converted to p-aminophenol by the alkaline phosphatase and the p-aminophenol formed is oxidized to form quinone imine in a redox reaction at electrodes of the microarray arrangement and the p-aminophenol/quinone imine redox pair is cyclized, which leads to a measurable current rise at the electrodes. This current rise (dI/dT) is proportional to the amount of bound PCR product.

The temperature is then increased step by step over a temperature range by approximately 20° C. to approximately 60° C., which leads to a progressive melting of the hybrids at relatively high temperatures (starting from approximately 25° C.), wherein the PCR products with single point mutations which have a mismatch in the hybrid melt significantly more rapidly than the "perfect match" hybrids, the wild type hybrids in the example. This results in a detectable signal difference between the wild type (perfect match) and the single point mutant (single base mismatch).

The summary of a plurality of experiments is illustrated in the curves 31a, 31b, 32a, 32b shown in FIGS. 5 and 6. The signal strength is illustrated as a function of the temperature. The curves 31a, 31b show the melting curves for FcV wild type and the curves 32a, 32b show the melting curves for FcV Leiden. It can readily be recognized that with the use of the method according to an embodiment of the invention with the added additive, the melting curves 31b, 32b (FIG. 6) are reproducible significantly better (that is to say lie closer together in each case for FcV wild type and FcV Leiden) and more distinctive signal differences result than without the use of the method according to an embodiment of the invention, 31a, 32a (FIG. 5). Primarily at relatively high temperatures (T>35° C.), the hybrids melt significantly more cleanly. One advantageous property of this method could be that the concentration of NaCl and EDTA in the chamber 140 (the detection chamber) rises during the hybridization.

It is emphasized that the example embodiment described is merely by way of example, and many kinds of variations with regard to the type and concentration of the additive, the type of detection and the reaction implementation are conceivable.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for analyzing nucleic acids in a microfluidic device, comprising:
   amplifying nucleic acids in a first chamber in the microfluidic device to produce an amplification crude product;
   contacting the amplification crude product with an additive including monovalent cations and an Mg2+ ion binding agent to form a mixture of the amplification crude product and the additive;
   wherein the additive is provided as a dry reagent in a second chamber in the microfluidic device; and wherein the additive is used to improve hybridization;
   and hybridizing the nucleic acids in the amplification crude product to at least one probe oligonucleotide without having first purified the nucleic acids from the amplification crude product.

2. The method as claimed in claim 1, wherein the monovalent cations are provided in the form of Na+ ions.

3. The method as claimed in claim 1, wherein the Mg2+ ion binding agent is EDTA.

4. The method as claimed in claim 1, wherein, prior to contacting the additive with the amplification crude product, a solvent is introduced into the second chamber.

5. The method as claimed in claim 4, wherein the additive is transferred in dissolved form from the second to the first chamber in order to contact the additive with the amplification crude product amplified.

6. The method as claimed in claim 1, wherein the amplification crude product is transferred from the first to the second chamber in order to contact the additive with the amplification crude product.

7. The method as claimed in claim 1, wherein the nucleic acids are amplified by way of PCR reaction.

8. The method as claimed in claim 1, wherein the at least one probe oligonucleotide is immobilized in the form of a microarray arrangement on a carrier.

9. The method as claimed in claim 1, wherein the nucleic acids hybridized to the probe oligonucleotide are detected.

10. The method as claimed in claim 9, wherein the nucleic acids are labeled and the detection is effected using the label.

11. The method as claimed in claim 10, wherein the label is an optical label.

12. The method as claimed in claim 10, wherein the label is an enzymatic label.

13. The method as claimed in claim 12, wherein the label catalyzes an enzymatic reaction which is optically detectable.

14. The method as claimed in claim 12, wherein the label catalyzes an enzymatic reaction which is electrochemically detectable.

15. The method as claimed in claim 14, wherein the electrochemical detection involves a current measurement amplified by way of redox cycling.

16. The method as claimed in claim 1, wherein the additive further comprises a binder.

17. The method as claimed in claim 2, wherein the Mg2+ ion binding agent is EDTA.

* * * * *